(12) United States Patent  (10) Patent No.: US 8,304,598 B2
Mosbacher et al.  (45) Date of Patent: Nov. 6, 2012

(54) GARMENTS WITH EASY-TO-USE SIGNALING DEVICE

(75) Inventors: Richard D. Mosbacher, Neenah, WI (US); Christopher P. Olson, Neenah, WI (US); Robert Schlaupitz, New London, WI (US); Andrew M. Long, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1560 days.

(21) Appl. No.: 11/303,222

(22) Filed: Dec. 15, 2005

(65) Prior Publication Data

US 2007/0142796 A1   Jun. 21, 2007

(51) Int. Cl.
*A61F 13/15* (2006.01)
(52) U.S. Cl. .... 604/361; 604/366; 604/367; 604/385.01
(58) Field of Classification Search .................. 604/361, 604/366, 367, 385.01
See application file for complete search history.

(56) References Cited

U.S. PATENT DOCUMENTS

| | | | |
|---|---|---|---|
| 3,759,246 A | 9/1973 | Flack et al. | |
| 3,864,676 A | 2/1975 | Macias et al. | |
| 4,100,324 A | 7/1978 | Anderson et al. | |
| 4,106,001 A | 8/1978 | Mahoney | |
| 4,191,950 A | 3/1980 | Levin et al. | |
| 4,205,672 A | 6/1980 | Dvorak | |
| 4,356,818 A | 11/1982 | Macias et al. | |
| 4,539,559 A | 9/1985 | Kelly et al. | |
| 4,653,491 A | 3/1987 | Okada et al. | |
| 4,704,108 A | 11/1987 | Okada et al. | |
| 4,704,116 A | 11/1987 | Enloe | |
| 4,768,023 A | 8/1988 | Xie | |
| 4,798,603 A | 1/1989 | Meyer et al. | |
| 4,940,464 A | 7/1990 | Van Gompel et al. | |
| 5,176,672 A | 1/1993 | Bruemmer et al. | |
| 5,266,928 A | 11/1993 | Johnson | |
| 5,284,703 A | 2/1994 | Everhart et al. | |
| 5,350,624 A | 9/1994 | Georger et al. | |
| 5,392,032 A * | 2/1995 | Kline et al. | ................... 340/604 |
| 5,459,452 A | 10/1995 | Deponte | |
| 5,486,166 A | 1/1996 | Bishop et al. | |
| 5,490,846 A | 2/1996 | Ellis et al. | |

(Continued)

FOREIGN PATENT DOCUMENTS

EP    1 047 033 A1   10/2000

(Continued)

OTHER PUBLICATIONS

"Anti-Static Wrist Straps," Internet web page "http://www.nc-corporation.com/WristStrap.asp", NC StatCorporation, Commack, NY, viewed and printed Apr. 29, 2005, pp. 1-5.

(Continued)

*Primary Examiner* — Jacqueline F. Stephens
(74) *Attorney, Agent, or Firm* — Randall W. Fieldhack

(57) ABSTRACT

Garments may include signaling devices. The signaling device may be configured to indicate to a user that a body fluid is present in the garment. The garment may include a chassis including an outer cover having an interior surface and an exterior surface. The chassis may include a crotch region positioned in between a front region and a back region. The garment may also include a signaling device including at least one first terminal and at least one second terminal.

27 Claims, 9 Drawing Sheets

U.S. PATENT DOCUMENTS

| | | |
|---|---|---|
| 5,509,915 A | 4/1996 | Hanson et al. |
| 5,557,263 A | 9/1996 | Fisher et al. |
| 5,760,694 A | 6/1998 | Nissim et al. |
| 5,766,389 A | 6/1998 | Brandon et al. |
| 5,790,036 A | 8/1998 | Fisher et al. |
| 5,808,554 A | 9/1998 | Shuminov |
| 5,820,973 A | 10/1998 | Dodge et al. |
| 5,838,240 A | 11/1998 | Johnson |
| 5,845,644 A | 12/1998 | Hughes et al. |
| 5,959,535 A | 9/1999 | Remsburg |
| 5,993,433 A | 11/1999 | St. Louis et al. |
| 6,075,178 A | 6/2000 | La Wilhelm et al. |
| 6,097,297 A | 8/2000 | Fard |
| 6,163,262 A | 12/2000 | Wu |
| 6,200,250 B1 | 3/2001 | Janszen |
| 6,246,330 B1 | 6/2001 | Nielsen |
| 6,248,097 B1 | 6/2001 | Beitz et al. |
| 6,399,853 B1 | 6/2002 | Roe et al. |
| 6,417,455 B1 | 7/2002 | Zein et al. |
| 6,501,002 B1 | 12/2002 | Roe et al. |
| 6,559,772 B2 | 5/2003 | Zand et al. |
| 6,573,837 B2 | 6/2003 | Bluteau |
| 6,580,013 B1 | 6/2003 | Belloso |
| 6,583,722 B2 | 6/2003 | Jeutter et al. |
| 6,603,403 B2 | 8/2003 | Jeutter et al. |
| 6,607,401 B1 | 8/2003 | Weaver et al. |
| 6,645,190 B1 | 11/2003 | Olson et al. |
| 7,053,781 B1 | 5/2006 | Haire et al. |
| 7,174,774 B2 | 2/2007 | Pawar et al. |
| 7,772,455 B1 | 8/2010 | Roe et al. |
| 7,834,234 B2 | 11/2010 | Roe et al. |
| 2002/0135489 A1 | 9/2002 | Chen et al. |
| 2003/0011479 A1 | 1/2003 | Bluteau |
| 2004/0036484 A1 | 2/2004 | Tamai |
| 2006/0244614 A1 | 11/2006 | Long |
| 2007/0049884 A1 | 3/2007 | Long et al. |
| 2007/0142797 A1 | 6/2007 | Long et al. |

FOREIGN PATENT DOCUMENTS

| | | |
|---|---|---|
| EP | 1 398 014 A2 | 3/2004 |
| FR | 2 788 430 A3 | 7/2000 |
| GB | 2 250 121 A | 5/1992 |
| JP | 10-151154 A | 6/1998 |
| WO | WO 84/01626 A1 | 4/1984 |
| WO | WO 96/20681 A1 | 7/1996 |
| WO | WO 97/42613 A2 | 11/1997 |
| WO | WO 98/12997 A1 | 4/1998 |
| WO | WO 99/51179 A1 | 10/1999 |
| WO | WO 00/37009 A2 | 6/2000 |
| WO | WO 02/101679 A1 | 12/2002 |
| WO | WO 2006/118913 A1 | 11/2006 |

OTHER PUBLICATIONS

"Duragrip Electrically Conductive Hook and Loop," Internet web page "http://www.hookandloop.com/site/product.cfm?id=electrically_conductive_hook_and_loop", Fastech of Jacksonville, Inc., viewed and printed Apr. 29, 2005, pp. 1-2.

"Surface Electrodes," Bio-logic® Systems Corp., catalog pp. 3-10, available prior to Dec. 15, 2005.

* cited by examiner

GARMENTS WITH EASY-TO-USE SIGNALING DEVICE

BACKGROUND OF THE INVENTION

Absorbent articles such as diapers, training pants, incontinence products, feminine hygiene products, swim undergarments, and the like conventionally include a liquid permeable body-side liner, a liquid impermeable outer cover, and an absorbent core. The absorbent core is typically located in between the outer cover and the liner for taking in and retaining liquids (e.g., urine) exuded by the wearer.

The absorbent core can be made of, for instance, superabsorbent particles. Many absorbent particles, especially super absorbent particles, are so efficient at absorbing liquids that it is sometimes difficult to tell whether or not the absorbent article has been insulted with a body fluid.

Accordingly, various types of moisture or wetness indicators have been suggested for use in absorbent articles. The wetness indicators may include alarm devices that are designed to assist parents or attendants to identify a wet diaper condition quickly upon insult. The devices produce either a visual or an audible signal.

In some embodiments, for instance, inexpensive conductive threads or foils have been placed in the absorbent articles. The conductive materials serve as conductive leads for a signaling device and form an open circuit in the article that can be closed when a body fluid, such as urine, closes the circuit. In these embodiments, although the absorbent articles may be disposable, the signaling devices are not. Thus, the signaling devices are intended to be removed from the article and reattached to a subsequent article.

Problems, however, have been encountered in designing an attachment mechanism for the signaling device that allows for a very reliable attachment of the signaling device to the conductive leads but does not appreciably increase the cost of the absorbent article. Further, problems have been experienced in designing an attachment mechanism that can be incorporated into the absorbent article during high speed manufacturing processes.

SUMMARY OF THE INVENTION

In general, the present disclosure is directed to garments with easy-to-use signaling devices. The signaling device, for instance, may be configured to indicate to a user that a body fluid is present in the absorbent article. For example, in one embodiment, the garment includes a chassis including an outer cover having an interior surface and an exterior surface. The chassis includes a crotch region positioned in between a front region and a back region. The front region and the back region jointly define a waist region. The garment includes first and second conductive elements contained in the chassis. The conductive elements are located in at least the waist region. The first and second conductive elements form part of a circuit. The garment also includes a signaling device including at least one first terminal and at least one second terminal. The first and second terminals are adapted to operatively connect to the first and second conductive elements. Further, the signaling device is adapted to connect to the chassis in at least three orientations. The first and second terminals operatively connect to the first and second conductive elements in each of the three orientations.

Another embodiment, the garment includes a chassis including an outer cover having an interior surface and an exterior surface. The chassis includes a crotch region positioned in between a front region and a back region. The front region and the back region jointly define a waist region. The garment includes first and second conductive elements contained in the chassis. The conductive elements are located in at least the waist region. The first and second conductive elements form part of a circuit. The garment also includes a signaling device including a first surface and a second surface. The first surface and the second surface being nonplanar. The first surface includes at least one first terminal, the second surface including at least one second terminal. The first and second terminals are adapted to operatively connect to the first and second conductive elements. Further the signaling device is adapted to connect to the garment in at least a first orientation and a second orientation. The first and second terminals operatively connect to the first and second conductive elements in the first and second orientations.

BRIEF DESCRIPTION OF THE DRAWINGS

The foregoing and other features and aspects of the present invention and the manner of attaining them will become more apparent, and the invention itself will be better understood by reference to the following description, appended claims and accompanying drawings, where:

Figure 1:
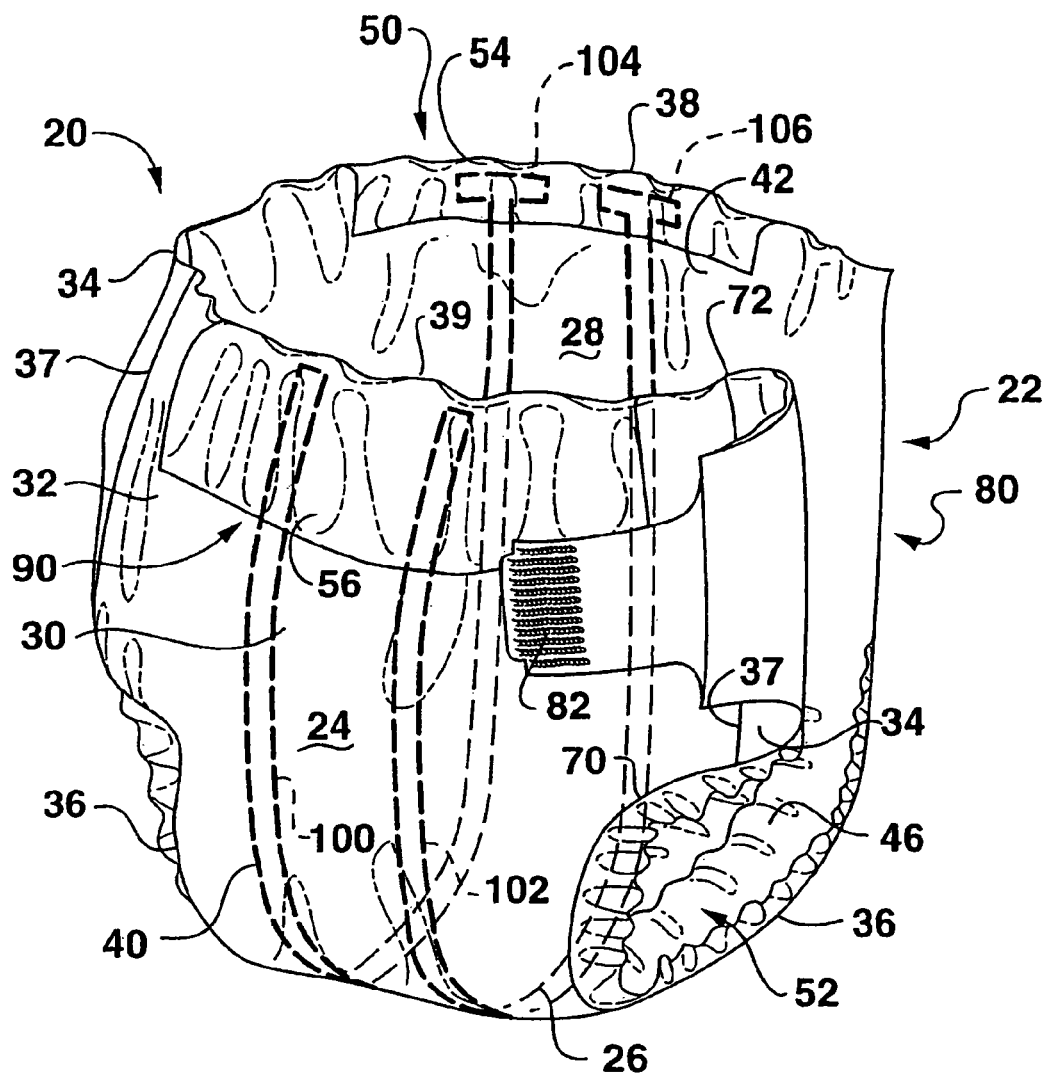
FIG. 1 is a rear perspective view of one embodiment of an absorbent article.

Repeat use of reference characters in the present specification and drawings is intended to represent the same or analogous features or elements of the present invention.

DETAILED DESCRIPTION OF THE INVENTION

It is to be understood by one of ordinary skill in the art that the present discussion is a description of exemplary embodiments only, and is not intended as limiting the broader aspects of the present invention.

The present disclosure is generally directed to absorbent articles adapted to be attached to a signaling device that may be configured to indicate the presence of a body fluid in the absorbent article or other changes in the condition of the product or wearer. The absorbent article may be, for instance, a diaper, a training pant, an incontinence product, a feminine hygiene product, a medical garment, a bandage, and the like. Absorbent articles may include an open circuit that becomes closed when a conductive fluid, such as a body fluid, is present in between a pair of conductive leads. Alternatively, absorbent articles may include a closed circuit that becomes open when a fluid, such as a body fluid, is present. Generally, the absorbent articles containing the circuit are disposable meaning that they are designed to be discarded after a limited use rather than being laundered or otherwise restored for reuse.

The circuit contained within the absorbent articles of the present disclosure is configured to be attached to a signaling device. The signaling device can provide power to the circuit while also including some type of audible, visible and/or electromagnetic signal that indicates to the user the presence of a body fluid. Although the absorbent article may itself be disposable, the signaling device may be reusable from article to article. In this regard, the present disclosure is particularly directed to different types of attachment mechanisms that allow easy connection between the circuit in the absorbent article and the signaling device.

As described above, the circuit in combination with the signaling device may be configured to indicate the presence of a body fluid contained within the absorbent article. The particular targeted body fluid may vary depending upon the particular type of absorbent article and the desired application. For instance, in one embodiment, the absorbent article comprises a diaper, a training pant, or the like and the signaling device is configured to indicate the presence of urine. Alternatively, the signaling device may be configured to indicate the presence of a metabolite that would indicate the presence of a diaper rash. For adult incontinence products and feminine hygiene products, on the other hand, the signaling device may be configured to indicate the presence of a yeast or of a particular constituent in urine or menses, such as a polysaccharide.

Figure 2:
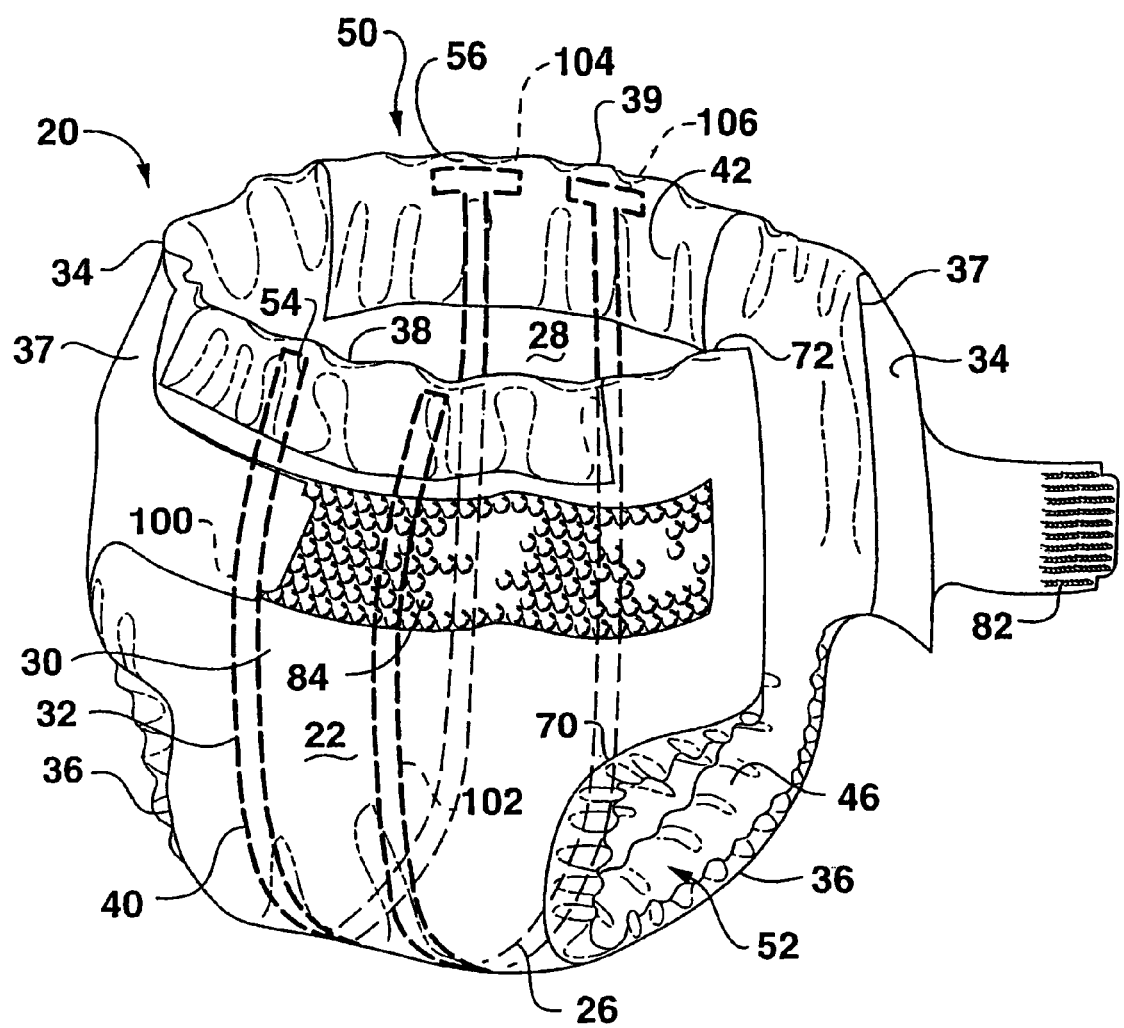
FIG. 2 is a front perspective view of the absorbent article illustrated in FIG. 1.

Referring to FIGS. 1 and 2, for exemplary purposes, an absorbent article 20 is shown. The absorbent article 20 may or may not be disposable. It is understood that the present invention is suitable for use with various other absorbent articles intended for personal wear, including but not limited to diapers, training pants, swim pants, feminine hygiene products, incontinence products, medical garments, surgical pads and bandages, other personal care or health care garments, and the like without departing from the scope of the present invention.

By way of illustration only, various materials and methods for constructing absorbent articles such as the diaper 20 of the various aspects of the present invention are disclosed in U.S. Pat. No. 4,798,603 issued Jan. 17, 1989, to Meyer et al.; U.S. Pat. No. 5,176,672 issued Jan. 5, 1993, to Bruemmer et al., U.S. Pat. No. 5,509,915 issued Apr. 23, 1996 to Hanson et al., U.S. Pat. No. 5,993,433 issued Nov. 30, 1999 to St. Louis et al., and U.S. Pat. No. 6,248,097 issued Jun. 19, 2001 to Beitz et al., PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Figure 3:
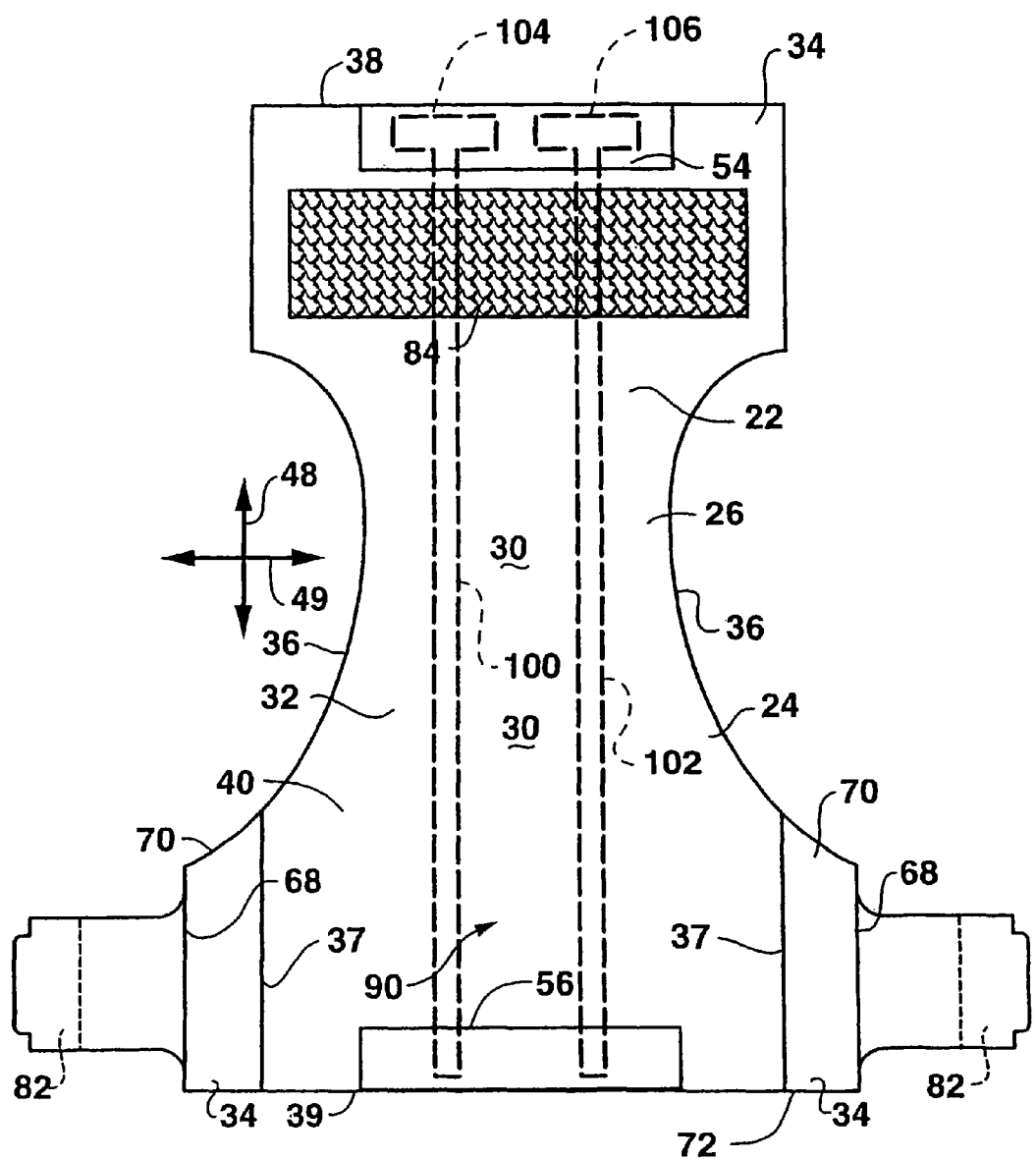
FIG. 3 is a plan view of the absorbent article shown in FIG. 1 with the article in an unfastened, unfolded and laid flat condition showing the surface of the article that faces away from the wearer.
Figure 4:
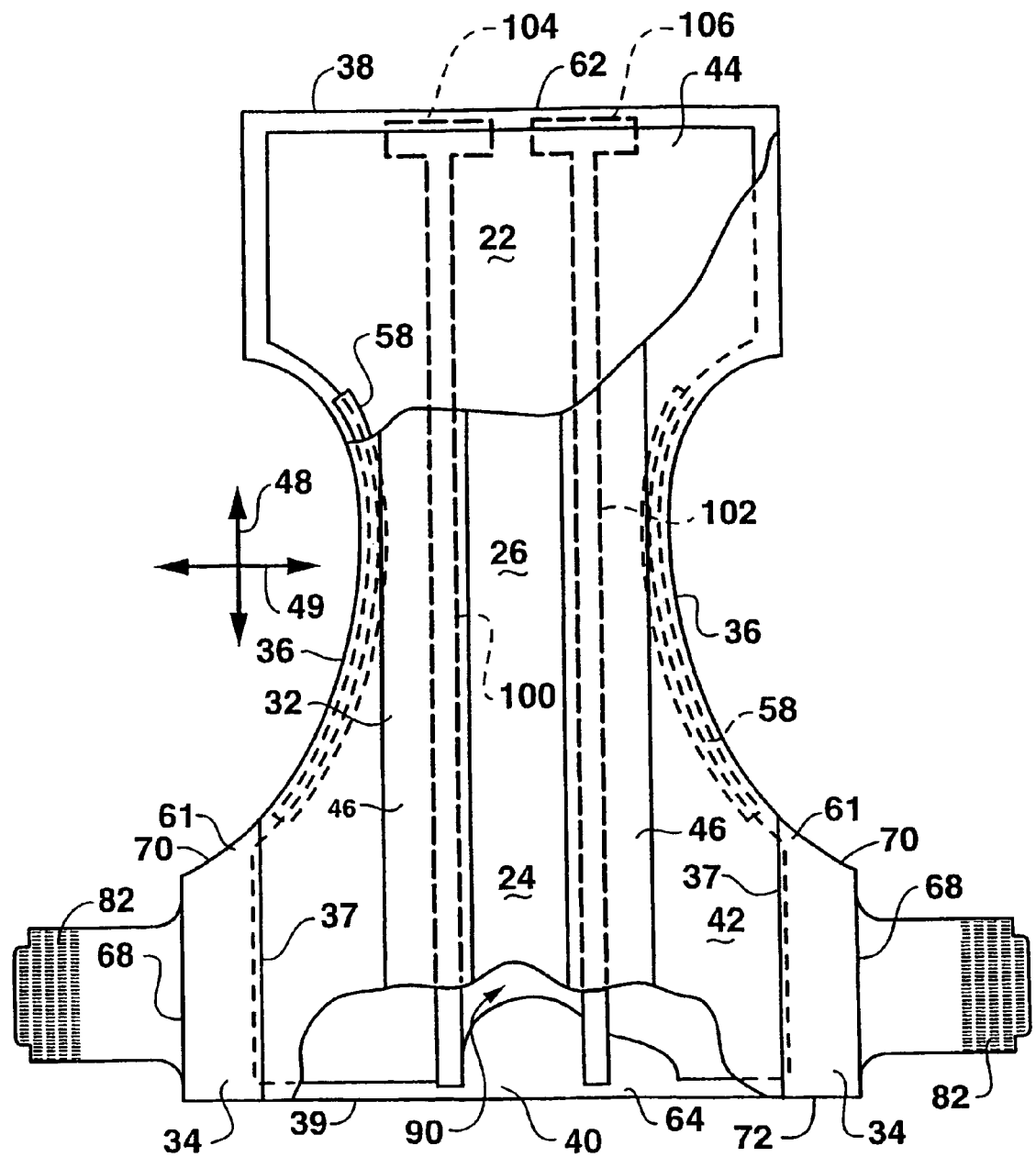
FIG. 4 is a plan view similar to FIG. 3 showing the surface of the absorbent article that faces the wearer when worn and with portions cut away to show underlying features.

A diaper 20 is representatively illustrated in FIG. 1 in a partially fastened condition. The diaper 20 shown in FIGS. 1 and 2 is also represented in FIGS. 3 and 4 in an opened and unfolded state. Specifically, FIG. 3 is a plan view illustrating the exterior side of the diaper 20, while FIG. 4 illustrates the interior side of the diaper 20. As shown in FIGS. 3 and 4, the diaper 20 defines a longitudinal direction 48 that extends from the front of the article when worn to the back of the article. Opposite to the longitudinal direction 48 is a lateral direction 49.

The diaper 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The diaper 20 also defines an inner surface 28 adapted in use (e.g., positioned relative to the other components of the article 20) to be disposed toward the wearer, and an outer surface 30 opposite the inner surface. The front and back regions 22, 24 are those portions of the diaper 20, which when worn, wholly or partially cover or encircle the waist or mid-lower torso of the wearer. The crotch region 26 generally is that portion of the diaper 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated diaper 20 includes a chassis 32 that, in this embodiment, encompasses the front region 22, the back region 24, and the crotch region 26. Referring to FIGS. 1-4, the chassis 32 includes an outer cover 40 and a bodyside liner 42 (FIGS. 1 and 4) that may be joined to the outer cover 40 in a superimposed relation therewith by adhesives, ultrasonic bonds, thermal bonds or other conventional techniques. Referring to FIG. 4, the liner 42 may suitably be joined to the outer cover 40 along the perimeter of the chassis 32 to form a front waist seam 62 and a back waist seam 64. As shown in FIG. 4, the liner 42 may suitably be joined to the outer cover 40 to form a pair of side seams 61 in the front region 22 and the back region 24. The liner 42 can be generally adapted, i.e., positioned relative to the other components of the article 20, to be disposed toward the wearer's skin during wear of the absorbent article. The chassis 32 may further include an absorbent structure 44 particularly shown in FIG. 4 disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

The elasticized containment flaps 46 as shown in FIG. 4 define a partially unattached edge which assumes an upright configuration in at least the crotch region 26 of the diaper 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the diaper 20 may also suitably include leg elastic members 58 (FIG. 4), as are known to those skilled in the art. The leg elastic members 58 can be operatively joined to the outer cover 40 and/or the bodyside liner 42 and positioned in the crotch region 26 of the absorbent article 20.

The leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 58 may include a plurality of dry-spun coalesced multifilament spandex elastomeric threads sold under the trade name LYCRA and available from Invista, Wilmington, Del. U.S.A.

In some embodiments, the absorbent article 20 may further include a surge management layer (not shown) which may be optionally located adjacent the absorbent structure 44 and attached to various components in the article 20 such as the absorbent structure 44 or the bodyside liner 42 by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference herein to the extent they are consistent (i.e., not in conflict) herewith.

As shown in FIGS. 1-4, the absorbent article 20 further includes a pair of opposing elastic side panels 34 that are attached to the back region of the chassis 32. As shown particularly in FIGS. 1 and 2, the side panels 34 may be stretched around the waist and/or hips of a wearer in order to secure the garment in place. As shown in FIGS. 3 and 4, the elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques.

In an alternative embodiment, the elastic side panels may also be integrally formed with the chassis 32. For instance, the side panels 34 may comprise an extension of the bodyside liner 42, of the outer cover 40, or of both the bodyside liner 42 and the outer cover 40.

In the embodiments shown in the figures, the side panels 34 are connected to the back region of the absorbent article 20 and extend over the front region of the article when securing the article in place on a user. It should be understood, however, that the side panels 34 may alternatively be connected to the front region of the article 20 and extend over the back region when the article is donned.

With the absorbent article 20 in the fastened position as partially illustrated in FIGS. 1 and 2, the elastic side panels 34 may be connected by a fastening system 80 to define a 3-dimensional diaper configuration having a waist opening 50 and a pair of leg openings 52. The waist opening 50 of the article 20 is defined by the waist edges 38 and 39 which encircle the waist of the wearer.

In the embodiments shown in the figures, the side panels are releasably attachable to the front region 22 of the article 20 by the fastening system. It should be understood, however, that in other embodiments the side panels may be permanently joined to the chassis 32 at each end. The side panels may be permanently bonded together, for instance, when forming a training pant or absorbent swimwear.

The elastic side panels 34 each have a longitudinal outer edge 68, a leg end edge 70 disposed toward the longitudinal center of the diaper 20, and waist end edges 72 disposed toward a longitudinal end of the absorbent article. The leg end edges 70 of the absorbent article 20 may be suitably curved and/or angled relative to the lateral direction 49 to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present invention. As shown in FIG. 4, the outer edges 68 are generally parallel to the longitudinal direction 48 while the waist end edges 72 are generally parallel to the transverse axis 49. It should be understood, however, that in other embodiments the outer edges 68 and/or the waist edges 72 may be slanted or curved as desired. Ultimately, the side panels 34 are generally aligned with a waist region 90 of the chassis.

The fastening system 80 may include laterally opposite first fastening components 82 adapted for refastenable engagement to corresponding second fastening components 84. In the embodiment shown in the figures, the first fastening component 82 is located on the elastic side panels 34, while the second fastening component 84 is located on the front region 22 of the chassis 32. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration.

The fastening components 82, 84 may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include hook fasteners and the second fastening components 84 include complementary loop fasteners.

Alternatively, the first fastening components 82 may include loop fasteners and the second fastening components 84 may be complementary hook fasteners. In another aspect, the fastening components 82, 84 can be interlocking similar surface fasteners, or adhesive and cohesive fastening elements such as an adhesive fastener and an adhesive-receptive landing zone or material; or the like. One skilled in the art will recognize that the shape, density and polymer composition of the hooks and loops may be selected to obtain the desired level of engagement between the fastening components 82, 84. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In the embodiment shown in the figures, the fastening components 82 are attached to the side panels 34 along the edges 68. In this embodiment, the fastening components 82 are not elastic or extendable. In other embodiments, however, the fastening components may be integral with the side panels 34. For example, the fastening components may be directly attached to the side panels 34 on a surface thereof.

In addition to possibly having elastic side panels, the absorbent article 20 may include various waist elastic members for providing elasticity around the waist opening. For example, as shown in the figures, the absorbent article 20 can include a front waist elastic member 54 and/or a back waist elastic member 56.

As described above, the present disclosure is particularly directed to incorporating a body fluid indicating system, such as a wetness indicating system into the absorbent article 20. In this regard, as shown in FIGS. 1-4, the absorbent article 20 includes a first conductive element 100 spaced from a second conductive element 102. In this embodiment, the conductive elements extend from the front region 22 of the absorbent article to the back region 24 without intersecting. The conductive elements 100 and 102 can comprise any suitable conductive material, such as a conductive thread or a conductive foil for example include 112-S silver metallic conductive paste (ink) from Electroscience Laboratories, Inc. and conductive foil described in U.S. Pat. No. 6,417,455 issued Jul. 9, 2002 to Zein et. Al. The first conductive element 100 may not intersect the second conductive element 102 in order to form an open circuit that may be closed, for instance, when a conductive fluid is positioned in between the conductive elements. In other embodiments, however, the first conductive element 100 and the second conductive element 102 may be connected to a sensor within the chassis. The sensor may be used to sense changes in temperature or may be used to sense the presence of a particular substance, such as a metabolite.

In the embodiment shown in FIG. 1, the conductive elements 100 and 102 extend the entire length of the absorbent article 20. It should be understood, however, that in other embodiments the conductive elements may extend only to the crotch region 26 or may extend to any particular place in the absorbent article where a body fluid is intended to be sensed.

The conductive elements 100 and 102 may be incorporated into the chassis 32 at any suitable location as long as the conductive elements are positioned so as to contact a body fluid that is absorbed by the absorbent article 20. In this regard, the conductive elements 100 and 102 generally lie inside the outer cover 40. In fact, in one embodiment, the conductive elements 100 and 102 may be attached or laminated to the inside surface of the outer cover 40 that faces the absorbent structure 44. Alternatively, however, the conductive elements 100 and 102 may be positioned on the absorbent structure 44 or positioned on the liner 42.

The conductive element 100 and 102 may be connected directly to a signaling device, either through direct or indirect contact. The first conductive element 100 may be attached to a first conductive pad member 104, while the second conductive element 102 may be connected to a second conductive pad member 106. The pad members 104 and 106 may be provided for making a reliable connection between the open circuit formed by the conductive elements to a signaling device that is intended to be installed on the chassis by the consumer or manufacturer. The pad members 104 and 106 may create a target zone for attaching the signaling device and the conductive leads or elements.

The conductive pad members 104 and 106 may have a relatively large surface area in relation to the conductive elements 100 and 102. For example, the conductive pad members 104 and 106 may have a surface area of at least 1 $cm^2$, at least 2 $cm^2$, and, in one embodiment, at least 3 $cm^2$. For instance, in one embodiment, the surface area of each pad member may be from about 2 $cm^2$ to about 4 $cm^2$.

The position of the conductive pad members 104 and 106 on the absorbent article 20 can vary depending upon where it is desired to mount the signaling device. For instance, in FIGS. 1, 3 and 4, the conductive pad members 104 and 106 are positioned in the front region 22 along the waist opening of the article. In FIG. 2, on the other hand, the conductive pad members 104 and 106 are positioned in the back region 24 along the waist opening of the article. It should be appreciated, however, that in other embodiments, the absorbent article 20 may include conductive pad members being positioned at each end of each conductive element 100 and 102. In still other embodiments, it should be understood that the pad members may be located along the side of the article or towards the crotch region of the article.

The position of the conductive pad members 104 and 106 within the multiple layers of the chassis 32 may also vary depending upon where it is desired to connect the signaling device and the type of attachment mechanism used to make a connection with the signaling device. As described above, the pad members 104 and 106 are electrically connected to the conductive elements 100 and 102. Thus, in one embodiment, the pad members 104 and 106 are positioned below (toward the body side) at least one layer of the outer cover 40. Positioning the pad members 104 and 106 below at least one layer of material may provide various advantages in some embodiments. For instance, locating the pad members 104 and 106 below at least one layer of material within the chassis 32 protects the pad members during shipping and storage and from forming a short circuit during use especially if the pad members are located adjacent one another. Another benefit to placing the pad members under at least one layer of material is the ability to easily manufacture the absorbent article 20 at high machine speeds.

It should be understood, however, that in other embodiments the conductive pad members 104 and 106 may be positioned at an exterior surface of the chassis 32. For instance, the pad members 104 and 106 may be positioned on the outside surface or on the inside surface as desired.

Figure 5:
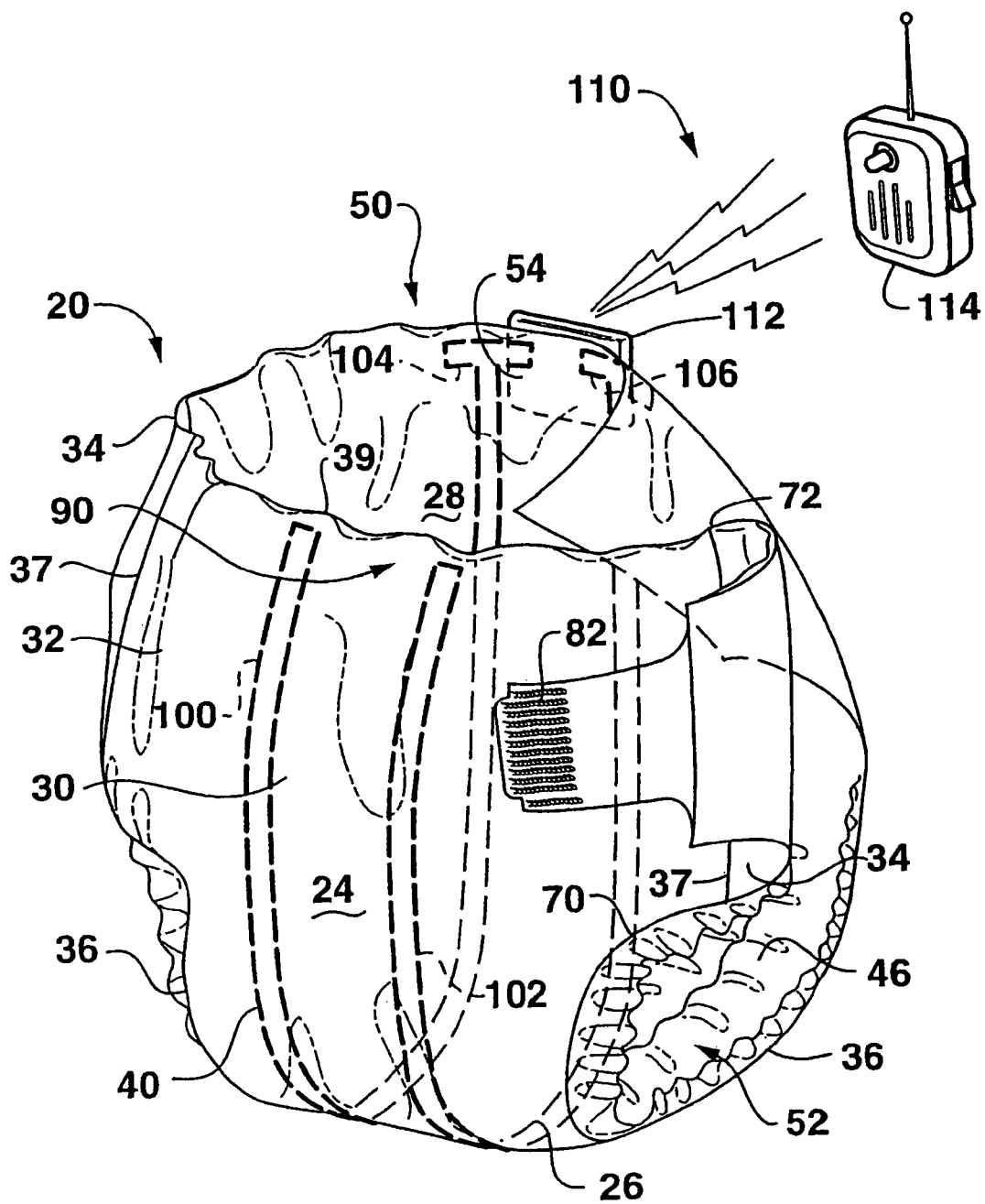
FIG. 5 is a perspective view of the embodiment shown in FIG. 1 further including one embodiment of a signaling device.

Referring to FIG. 5, for exemplary purposes, a signaling device 110 (as depicted by ref. numerals 112 and 114) is shown attached to the conductive pad members 104 and 106. As shown, in this embodiment, the signaling device generally 110 includes a transmitter 112 and a receiver 114. The transmitter 112 includes a pair of opposing terminals that are electrically connected to the corresponding conductive elements. When a body fluid is present in the absorbent article 20, the open circuit formed by the conductive elements 100 and 102 is closed which, in turn, activates the signaling device 110. In particular, in this embodiment, the transmitter 112 sends a wireless signal to the receiver 114 which then indicates to a user that a body fluid is present in the absorbent article.

The signaling device 110 can emit an audible signal or a visual signal in order to indicate to the user that the circuit has been closed. The audible signal, for instance, may be as simple as one or more beeps to perhaps emitting a musical tune. Similarly, if the signaling device 110 issues a visible signal, the visible signal may comprise a few lights or an interactive display. In still another embodiment, the receiver 114 of the signaling device 110 may be configured to vibrate when the circuit within the absorbent article is closed.

In the embodiment shown in FIG. 5, the signaling device 110 includes a transmitter 112 in combination with a receiver 114. It should also be understood, however, that the signaling device may comprise a single unit that remains attached to the absorbent article 20. For example, the signaling device may be mounted on the absorbent article and issue a visible signal and/or an audible signal from the article itself.

Attachment mechanisms between the conductive pad members or the conductive elements and the signaling device and the particular construction of the pad member for each embodiment will now be described in detail with respect to FIGS. 7-11. The signaling device 110 may connect to the to the chassis 40 in many different ways. The absorbent article 20 may include a signaling device receptacle 140 adapted to connect the signaling device 110 to the absorbent chassis 40. The signaling device 110 may connect to the chassis utilizing adhesives, cohesives, magnets, hook and loop, clips or snaps. Alternatively, the signaling device 110 may connect to the chassis 140 by capturing all or portions of the signaling device 110 in a pocket or utilizing elastic portions which wrap around the signaling device 110 maintaining it in place.

Figure 7:
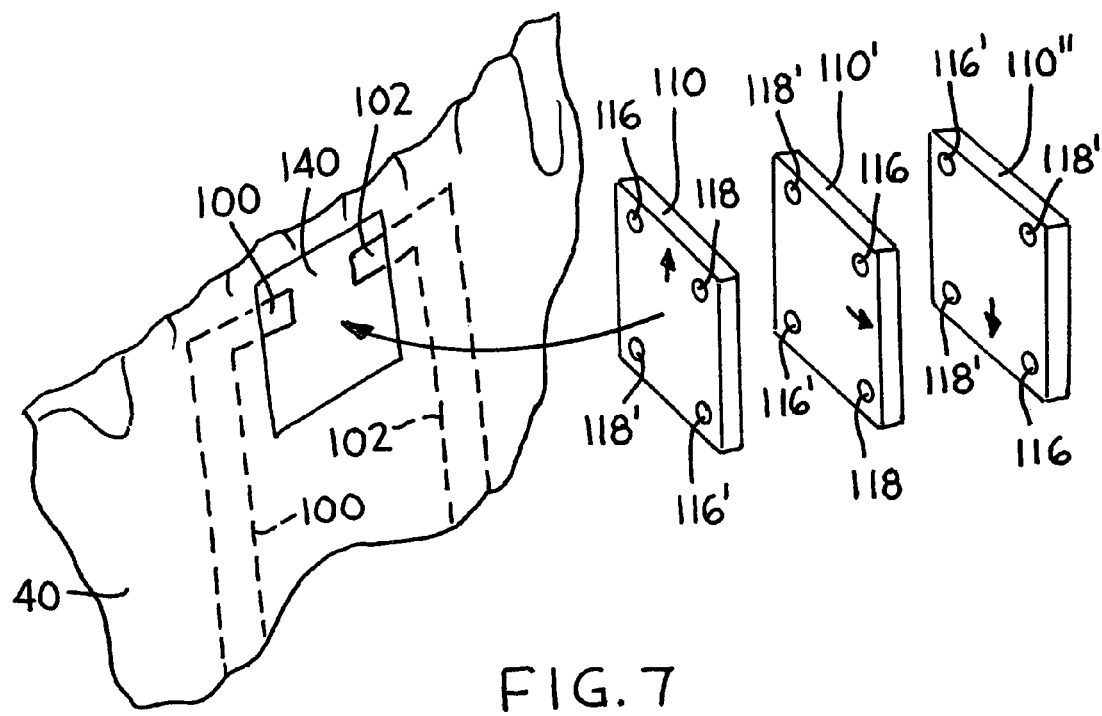
FIG. 7 is a perspective view of one embodiment of an attachment mechanism for a signaling device to the absorbent article.

The signaling device 110 includes first terminals 116, 116' and second terminals 118, 118'. As illustrated in FIG. 7, the first terminals 116, 116' and the second terminals 118, 118' are located on a primary surface of the signaling device 110. More specifically the primary surface of the signaling device 110 is roughly in the shape of a square and the first terminals 116, 116' are located diagonally opposite one another, one first terminal 116 located in the upper left hand quadrant of the square and the other first terminal 116' located in the lower right hand quadrant of the square. Further, the second terminals 118, 118' are also located diagonally opposite one another, one second terminal 118 located in the upper right hand quadrant of the square and the other second terminal 118' located in the lower left hand quadrant of the square. Additionally, the terminals 116, 116', 118, 118' are position similarly with respect to the edges of the signaling device 110.

The signaling device 110 may be adapted to connect to the article 20 in one, two, three, four, five, six, seven, eight or more distinct orientations. The design of the signaling device 110, the chassis 40, and receptacle 140 (if utilized) may be designed such that the first and second terminals 116, 116', 118, 118' operatively connect to the first and second conductive elements 100, 102 in one, two, three, four, five, six, seven, eight or more of the distinct orientations. This compatibility between the signaling device 110 and the chassis 40 may allow for quicker and less complicated connection of the signaling device 110. This feature may be very advantageous when applying a diaper or training pant to an active child, or while diapering during the night in low light.

As shown in FIG. 7, the first conductive element 100 is disposed in the upper left hand quadrant of the receptacle 140 and the second conductive element 102 is disposed in the upper right hand quadrant of the receptacle 140. Also shown in FIG. 7 is the signaling device 110 shown in a first orientation 110, a second orientation 110' and a third orientation 110", the second orientation 110' being a 90 degrees clockwise rotation of the first orientation 110, and the third orientation 110" being a 90 degree clockwise rotation of the second orientation 110'.

With the signaling device 110 positioned within receptacle 140 in a first orientation, as indicated by the arrow pointing upward, the first terminal 116 contacts the second conductive element 102 and the second terminal 118 contacts the first conductive element 100. Rotating the signaling device 110 90 degrees, results in a second orientation 110', as indicated by the arrow pointing to the right, with the second terminal 118' contacting the second conductive element 102 and first terminal 116 contacting the first conductive element 100. Rotating the signaling device 110' another 90 degrees, results in a third orientation 110", as indicated by the arrow pointing downward, with the first terminal 116' contacting the second conductive element 102 and second terminal 118' contacting the first conductive element 100. Not shown is the signaling device in a fourth orientation with the arrow pointing to the left. This embodiment illustrates a signaling device that is adapted to connect to the article 20 in four orientations. The first and second terminals 116, 116', 118, 118' operatively connect to the first and second conductive elements 100, 102 in each of the four orientations.

Figure 7A:
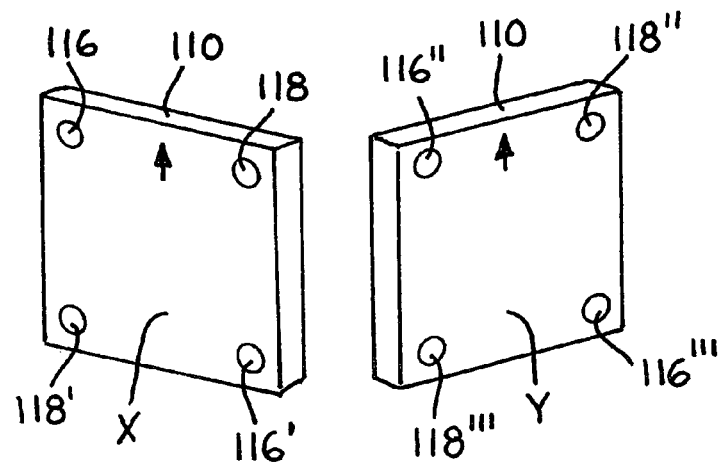
FIG. 7A is a side-by side view of the front in back of a single signaling device.

Shown in FIG. 7A is a side-by side view of the front in back of a single signaling device 110 which may be connected to the receptacle 140 shown in FIG. 7. FIG. 7A illustrates major surface X, and opposite major surface Y, of the signaling device 110. First Surface X is similar to the surface containing the terminals in FIG. 7. In addition, second surface Y includes first and second terminals positioned in similar locations as on the first surface X. Surface Y in FIG. 7A includes first terminals 116", 116'" and second terminals 118", 118'". The signaling device 110 illustrated in FIG. 7A may be connected to the receptacle 140 in 8 orientations, four orientations (90 degree rotations) on first surface X and four orientations (90 degree rotations) on second surface Y. This signaling device 110 may provide an advantage to a user, in that the user need not concern themselves with the orientation of the signaling device 140 when connecting it to the receptacle 140, and in particular even which surface X or Y is disposed toward the outer cover.

Figure 8:
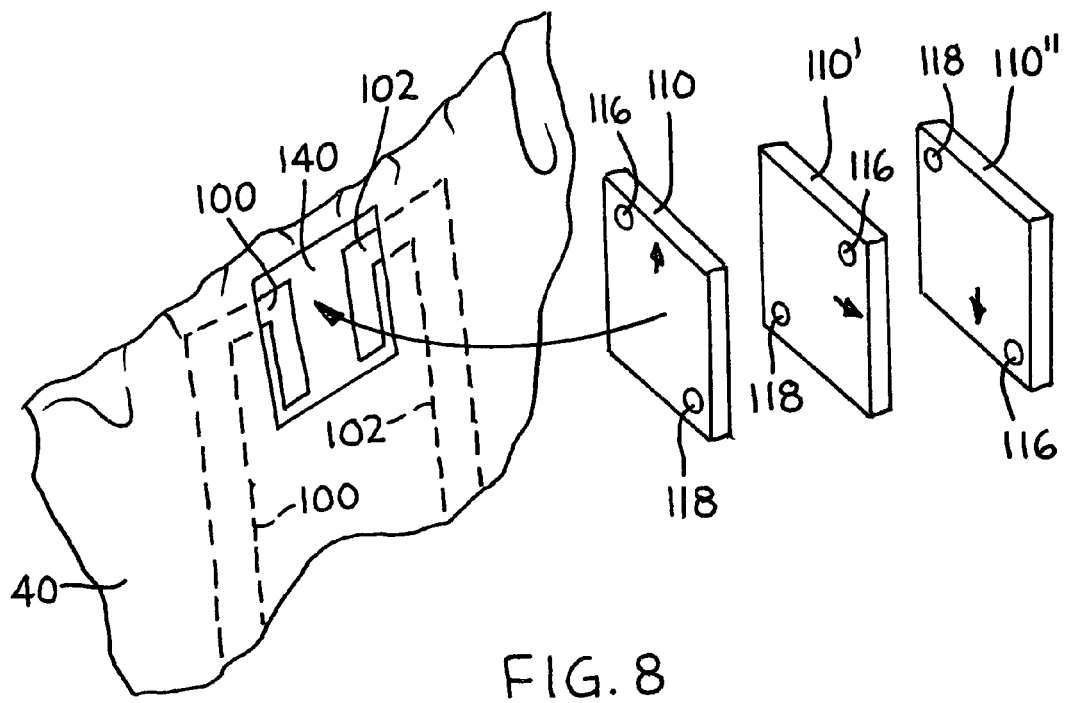
FIG. 8 is another embodiment of an attachment mechanism for attaching a signaling device to an absorbent article.

FIG. 8 illustrates a second embodiment where the first conductive element 100 is disposed in the left two quadrants of the receptacle 140 and the second conductive element 102 is disposed in the right two quadrants of the receptacle 140. The first conductive element 100 may extend within the receptacle adjacent the left edge of the receptacle over substantially the length of the edge. Similarly, the second conductive element 102 extends within the receptacle adjacent the right edge of the receptacle over substantially the length of the edge.

Also shown in FIG. 8 is the signaling device 110 shown in a first orientation 110, a second orientation 110' and a third orientation 110", the second orientation 110' being a 90 degrees clockwise rotation of the first orientation 110, and the third orientation 110" being a 90 degree clockwise rotation of the second orientation 110'.

As illustrated in FIG. 8, the first terminal 116 and the second terminal 118 are located on a primary surface of the signaling device 110. More specifically the primary surface of the signaling device 110 is roughly in the shape of a square and the first terminal 116 and the second terminal 118 are located diagonally opposite one another, the first terminal 116 located in the upper left hand quadrant of the square and the second terminal 118 located in the lower right hand quadrant of the square. Additionally, the terminals 116 and 118 are position similarly with respect to the edges of the signaling device 110. The terminals 116, 118 may be located on one major surface; alternatively the terminals 116, 118 may be located on both opposing major surfaces X, Y.

With the signaling device 110 positioned within the receptacle 140 in a first orientation, as indicated by the arrow pointing upward, the first terminal 116 contacts the second conductive element 102 and the second terminal 118 contacts the first conductive element 100. Rotating the signaling device 110 90 degrees, results in a second orientation 110', as indicated by the arrow pointing to the right, with the first terminal 116 contacting the first conductive element 100 and second terminal 118 contacting the second conductive element 102. Rotating the signaling device 110' another 90 degrees, results in a third orientation 110", as indicated by the arrow pointing downward, with the first terminal 116 contacting the first conductive element 100 and second terminal 118 contacting the second conductive element 102. Not shown is the signaling device in a fourth orientation with the arrow pointing to the left. The embodiment illustrates a signaling device that is adapted to connect to the article 20 in four orientations. The first and second terminals 116, 118 operatively connecting to the first and second conductive elements 100, 102 in each of the four orientations.

Figure 9:
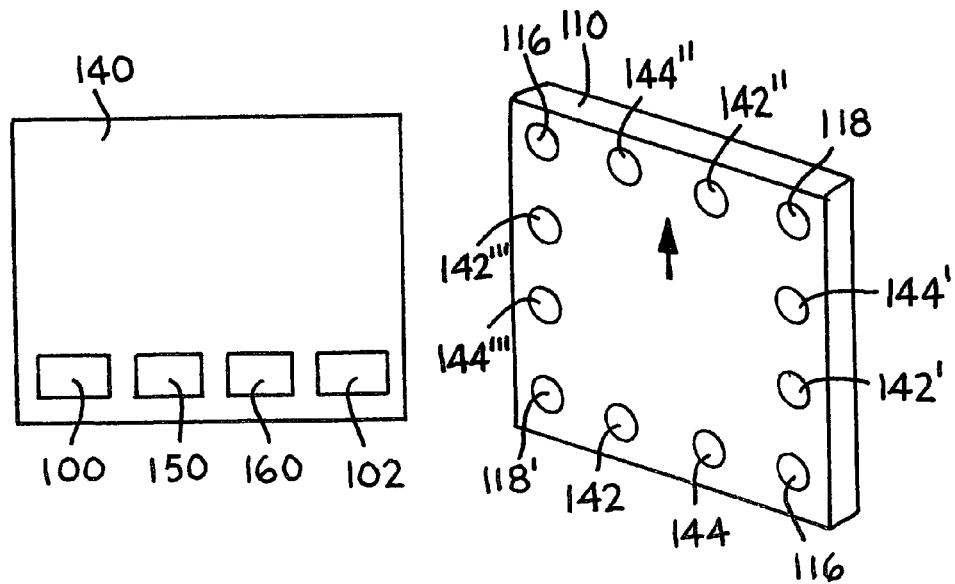
FIG. 9 is still another embodiment of an attachment mechanism for attaching a signaling device to an absorbent article.

FIG. 9 illustrates a signaling device receptacle 140 and a signaling device 110. The receptacle 140 includes first 100, second 102, third 150 and fourth 160 conductive elements positioned along an edge of the receptacle 140, the elements 100, 102, 150, and 160 being equally spaced apart. The signaling device 110 includes first 116, 116', second 118, 118', third 142, 142', 142", 142''', and fourth 144, 144", 144", 144''' terminals. The first 116, 116' and second 118, 118' terminals are located as described according to FIG. 7 generally in the corners of the signaling device 110. Further, along each edge, located between first 116, 116' and second terminals 118, 118' are a third terminal and a fourth terminal. More specifically, alone each edge, space substantially equally along the edge, are a first, second, third, and forth terminals. The first and second terminals are located in the first position on the edge and the last position on the edge and the third and fourth terminals are located in between the first and second terminals.

With the signaling device 110 in a the orientation as shown, as indicated by the arrow pointing upward, the first terminal 116' contacts the first conductive element 100 and the second terminal 118' contacts the second conductive element 102. Additionally, the third terminal 142 contacts the fourth conductive element 160 and the fourth terminal 144 contacts the third conductive element 144. Rotating the signaling device as described above with reference with FIG. 7 will produce the connections as described above. Further, in each of the four orientations produced by rotating the signaling device successively 90, the third conductive element 150 will contact the fourth terminal 144, 144', 144" or 144''', and the fourth conductive element 160 will contact the third terminal 142, 142', 142" or 142'''.

Figure 10:
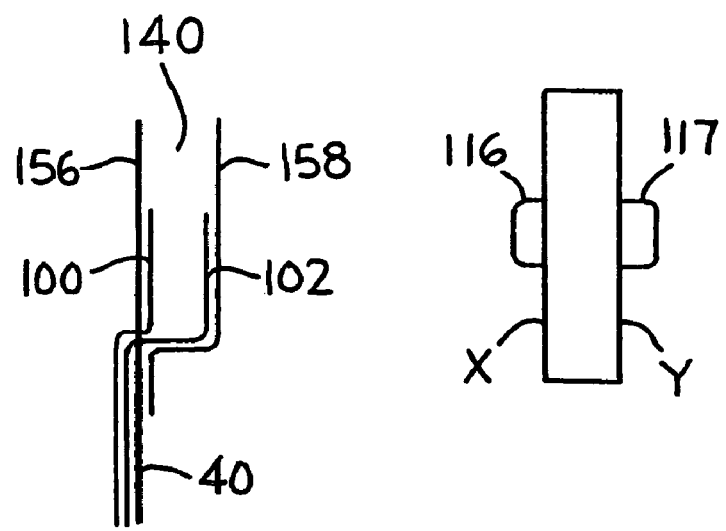
FIG. 10 is a side view of another embodiment of an attachment mechanism for attaching a signaling device to an absorbent article.

FIG. 10 illustrates a sectional side view of a signaling device receptacle 140 and a signaling device 110. The receptacle 140 includes first 100 and second 102 conductive elements and a first material 156 joined to a second material 158. The first material 156 may be a first layer of outer cover 40 and the second material may be a second layer of the outer cover 40. Alternatively, the first material 156 may be the outer cover 40 and the second material may be an additional piece of material joined to the outer cover 40. As shown in FIG. 10, the first conductive element 100 is connected to the first material 156, and the second conductive element is connected to the second material 158. More specifically, the first and second conductive elements 100, 102 are positioned on the inside walls of receptacle 140 and at least in middle of the receptacle 140 and opposite one another.

The signaling device 110 includes first 116 and second 118 terminals. The first terminal 116 may be located centrally on a first surface X of the signaling device 110 and the second terminal 118 may be centrally located on a second surface Y of the signaling device 110. The first 116 and second terminal 118 are sized to make contact with the first and second terminal 100, 102, when the signaling device 110 is position in the receptacle 140.

With the first surface X facing the first material 156, the first terminal 116 connects to the first conductive element 100 and the second terminal 118 connects to the second conductive element 102. The signaling device 110 may be rotated about an axis located between the two terminals while maintaining this connectivity. A square signaling device 110 will have a first, second, third and forth orientation with this connectivity.

With the second surface Y facing the first material 156, the first terminal 116 connects to the second conductive element 102 and the second terminal 118 connects to the first conductive element 100. The signaling device 110 may be rotated about an axis located between the two terminals while maintaining this connectivity. A square signaling device 110 will have a fifth, sixth, seventh and eighth orientation with this connectivity.

This configuration of the receptacle 140 and signaling device 110 eliminates the need for the user to determine the front of the signaling device 110 from the back or any rotational position with respect to a top edge. The signaling device 110 may be square, rectangular, triangular, circular or any other shape that may be appealing to a user.

Figure 11:
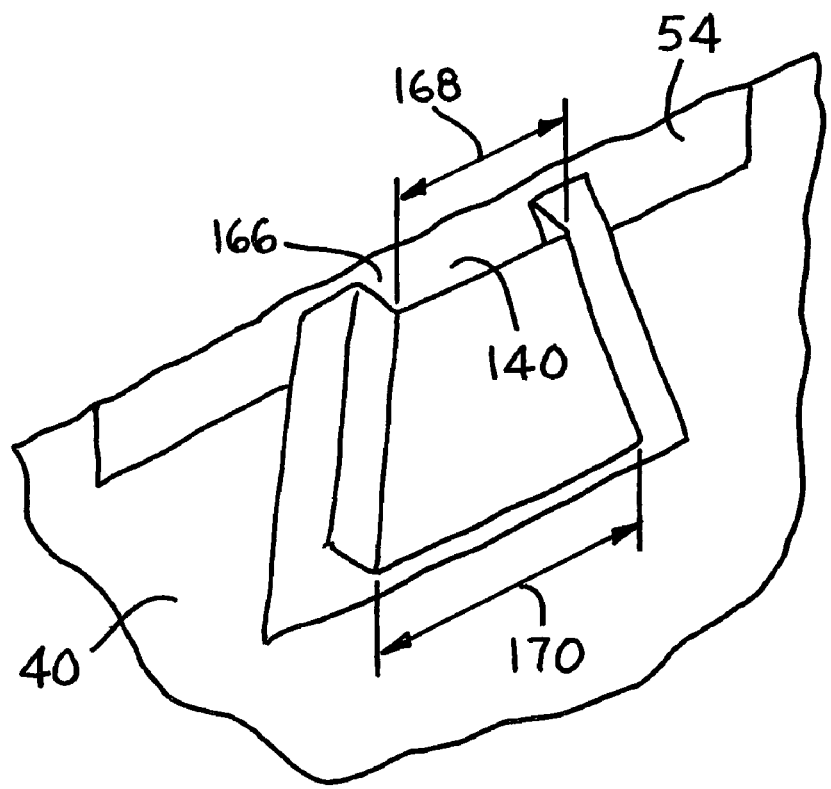
FIG. 11 is a perspective view of another embodiment of an attachment mechanism for attaching a signaling device to an absorbent article.

FIG. 11 illustrates a signaling device receptacle 140 which defines a pocket having an open edge 166. The signaling device may pass through the open edge 166 to enter the receptacle 140. The receptacle 140 defining the pocket may be formed from a single piece of material folded over upon it self to create the pocket. Alternatively, the receptacle 140 defining the pocket may be formed from two or more pieces of material joined together to create the pocket. The open edge 166 of the receptacle 140 may be elasticized to aid in maintaining the signaling device 110 in the receptacle 140. The open edge 166 may be elasticized by a waist elastic member component 54 or 56. Alternatively, the open edge 166 may be elasticized by one of the materials forming the pocket. The open edge 166 may have a width 168, and the pocket may have a maximum width 170 parallel to the open edge. The open edge width 168 before stretching may be less than the maximum width 170, alternatively, the open edge width 168 before stretching may be less than 90%, or 75% of the maximum width 170. The maximum width 170 may be determined by the specific signaling device, being slightly smaller or slightly larger than signaling device. This feature may act to push the signaling device 110 into the pocket during use, thereby reducing the chance the signaling device 110 may fall out and become inoperative.

Figure 6:
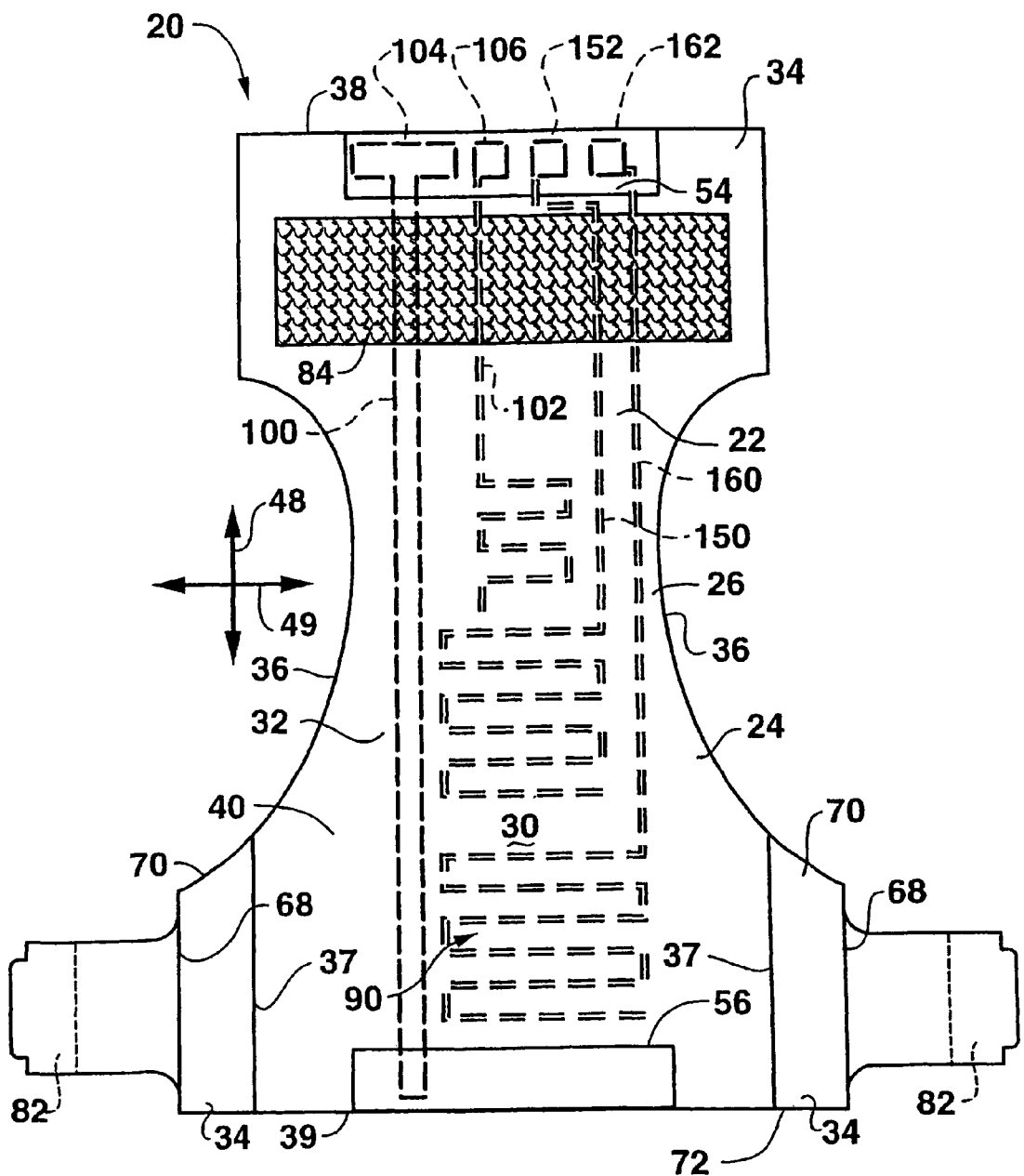
FIG. 6 is a plan view of another embodiment of an absorbent article illustrating the article in an unfastened, unfolded and laid flat condition illustrating the surface of the article that faces away from the wearer.

Referring to FIG. 6, still another embodiment of an absorbent article 20 made in accordance with the present invention is shown. In the embodiment illustrated in FIG. 6, in addition to the first conductive element 100 and the second conductive element 102, the absorbent article includes a third conductive element 150 and a fourth conductive element 160. As illustrated, the first conductive element 100 extends the entire length of the absorbent article. The second conductive element 102, however, is located primarily within the front region of the chassis. The third conductive element 150 passes through the front region and is primarily located in the crotch region of the chassis.

Finally, the fourth conductive element 160 extends through the front region and the crotch region and then is primarily located in the back region of the chassis.

Similar to the conductive elements 100 and 102, the third conductive element 150 may be connected to a third conductive pad member 152, while the fourth conductive element 160 may be connected to a fourth conductive pad member 162.

In the embodiment illustrated in FIG. 6, the additional conductive elements are used for not only indicating the presence of a body fluid but also indicating the location of the body fluid. For instance, if the body fluid is located in the front region, the circuit between the first conductive element 100 and the second conductive element 102 is closed. If the body fluid is contained in the crotch region, on the other hand, the circuit formed between the third conductive element 150 and the first conductive element 100 becomes closed. In similar fashion, if the body fluid is located in the back region, the circuit becomes closed between the fourth conductive element 160 and the first conductive element 100.

The embodiment illustrated in FIG. 6 is intended to be placed in conjunction with a signaling device that includes four corresponding terminals for each of the four conductive pad members. The signaling device can then be configured to not only indicate when a body fluid is present but also indicate which circuits are closed, thus indicating the location of the body fluid in addition to its mere presence.

The remaining materials used to form the absorbent article 20 that surround the signaling device receptacle 140 may vary depending upon the particular application and the particular product being produced.

The outer cover 40, for instance, may be breathable and/or may be liquid impermeable. The outer cover 40 may be constructed of a single layer, multiple layers, laminates, spunbond fabrics, films, meltblown fabrics, elastic netting, microporous webs, bonded card webs or foams provided by elastomeric or polymeric materials. The outer cover 40, for instance, can be a single layer of a liquid impermeable material, or alternatively can be a multi-layered laminate structure in which at least one of the layers is liquid impermeable. In other embodiments, however, it should be understood that the outer cover may be liquid permeable. In this embodiment, for instance, the absorbent article may contain an interior liquid barrier layer.

For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Bostik Findley Adhesives, Inc., of Wauwatosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polypropylene nonwoven web. The outer layer may also be made of those materials of which the liquid permeable bodyside liner 42 is made.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. A suitable bodyside liner 42 may be manufactured from a wide selection of web materials, such as porous foams, reticulated foams, apertured plastic films, woven and non-woven webs, or a combination of any such materials. For example, the bodyside liner 42 may include a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The absorbent structure 44 may be disposed between the outer cover 40 and the bodyside liner 42. The absorbent structure 44 can be any structure or combination of components which are generally compressible, conformable, non-irritating to a wearer's skin, and capable of absorbing and retaining liquids and certain body wastes. For example, the absorbent structure 44 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular aspect, the absorbent web material is a matrix of cellulosic fluff and superabsorbent hydrogel-forming particles. The cellulosic fluff may include a blend of wood pulp fluff. One preferred type of fluff is identified with the trade designation CR 1654, available from Bowater of Greenville, S.C., USA, and is a bleached, highly absorbent sulfate wood pulp containing primarily southern soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art. Furthermore, the absorbent structure may itself encompass multiple layers in the Z direction. Such multiple layers may take advantage of differences in absorbency capacity, such as by placing a lower capacity absorbent material layer closer to the liner 42 and a higher capacity absorbent material closer to the outer cover layer 40. Likewise, discrete portions of an absorbent single-layered structure may encompass higher capacity absorbents, and other discrete portions of the structure may encompass lower capacity absorbents.

As a general rule, the superabsorbent material is present in the absorbent web in an amount of from about 0 to about 90 weight percent based on total weight of the web. The web may have a density within the range of about 0.10 to about 0.60 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and desirably is capable of absorbing more than about 25 times its weight in liquid. Suitable superabsorbent materials are readily available from various suppliers. For example, SXM 9394, and Favor 9543 superabsorbents are available from DeGussa Superabsorbers.

After being formed or cut into a desired shape, the absorbent web material may be wrapped or encompassed by a suitable tissue or meltblown web or the like wrap sheet that aids in maintaining the integrity and shape of the absorbent structure 44.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. Nos. 4,100,324 to Anderson, et al.; 5,284,703 to Everhart, et al.; and 5,350,624 to Georger, et al.; which are incorporated herein by reference to the extent they are consistent (i.e., not in conflict) herewith.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A garment comprising:
   a chassis comprising an outer cover having an interior surface and an exterior surface, the chassis including a crotch region positioned in between a front region and a back region, the front region and the back region jointly defining a waist region;
   first and second conductive elements contained in the chassis, the conductive elements located in at least the waist region, the first and second conductive elements forming part of a circuit; and
   a signaling device including at least one first terminal and at least one second terminal, the first and second terminals adapted to operatively connect to the first and second conductive elements;
   wherein the signaling device is adapted to connect to the chassis in at least three orientations, the first and second terminals operatively connect to the first and second conductive elements in each of the three orientations.

2. The garment of claim 1 further comprising a first conductive pad member electrically connected to the first conductive element and a second conductive pad member electrically connected to the second conductive element, the conductive pad members being positioned below at least one layer of material of the chassis, the conductive pad members each being configured to electrically connect the conductive elements to the terminals.

3. The garment of claim 1 further comprising an absorbent structure positioned adjacent the interior surface of the outer cover.

4. The garment of claim 1 wherein the signaling device produces an audible signal, a visible signal, or vibrates upon completion of the circuit.

5. The garment of claim 1 wherein the signaling device comprises a transmitter and a receiver, wherein, the transmitter sends a wireless signal to the receiver which produces an audible or visible signal when the signaling device is activated.

6. The garment of claim 1 further comprising a third conductive element that extends into the back region of the chassis and a fourth conductive element that extends into the front region of the chassis, the signaling device further including at least one third terminal and at least one fourth terminal, the third and fourth terminals adapted to operatively connect to the third and fourth conductive elements, when the substance is present in the back region of the chassis, the first and third conductive elements form a closed circuit, and when the substance is present in the front region, the fourth and first conductive elements forms a closed circuit.

7. The garment of claim 1 wherein the first and second conductive elements extend from the waist region to the crotch region without intersecting.

8. The garment of claim 1 wherein the first and second conductive elements form an open circuit and wherein, when a body fluid is present between the first and second conductive elements, the body fluid closes the circuit to activate the signaling device.

9. The garment of claim 1 wherein the chassis includes a signaling device receptacle adapted to contain the signaling device, the receptacle defining a pocket having an open edge, the open edge being elasticized.

10. The garment of claim 1 wherein the chassis includes a signaling device receptacle adapted to contain the signaling device, the receptacle defining a pocket having an open edge having an open edge width and the pocket having a maximum width parallel to the open edge, the open edge width being less than the maximum width.

11. The garment of claim 10 wherein the open edge width is less than 90 percent the maximum width.

12. The garment of claim 1 wherein the chassis includes a signaling device receptacle adapted to contain the signaling device, the receptacle comprising a first material and a second material joined to the first material, the first conductive element connected to the first material, the second conductive element connected to the second material.

13. The garment of claim 12 wherein the signaling device includes a first surface and a second surface, the first surface and the second surface being nonplanar, the first surface including the first terminal and the second surface including the second terminal.

14. A garment comprising:
   a chassis comprising an outer cover having an interior surface and an exterior surface, the chassis including a crotch region positioned in between a front region and a back region, the front region and the back region jointly defining a waist region;
   first and second conductive elements contained in the chassis, the conductive elements located in at least the waist region, the first and second conductive elements forming part of a circuit; and
   a signaling device including a first surface and a second surface, the first surface and the second surface being nonplanar, the first surface including at least one first terminal, the second surface including at least one second terminal, the first and second terminals adapted to operatively connect to the first and second conductive elements;
   wherein the signaling device is adapted to connect to the garment in at least a first orientation and a second orientation, where the first and second terminals operatively connect to the first and second conductive elements in the first and second orientations.

15. The garment of claim 14 further comprising a first conductive pad member electrically connected to the first conductive element and a second conductive pad member electrically connected to the second conductive element, the conductive pad members each being configured to electrically connect the conductive elements to the terminals.

16. The garment of claim 14 wherein the signaling device further comprises at least one second terminal on the first surface and at least one first terminal on the second surface wherein the first and second terminals on the first surface connect to the first and second conductive elements in the first orientation and the first and second terminals on the second surface connect to the first and second conductive elements in the second orientation.

17. The garment of claim 14 further comprising an absorbent structure positioned adjacent the interior surface of the outer cover.

18. The garment of claim 14 wherein the signaling device produces an audible signal, a visible signal, or vibrates when activated.

19. The garment of claim 14 wherein the signaling device comprises a transmitter and a receiver, wherein, the transmitter sends a wireless signal to the receiver which produces an audible or visible signal when the signaling device is activated.

20. The garment of claim 14 further comprising a third conductive element that extends into the back region of the chassis and a fourth conductive element that extends into the front region of the chassis, the signaling device further including at least one third terminal and at least one fourth terminal, the third and fourth terminals adapted to operatively connect to the third and fourth conductive elements, when the substance is present in the back region of the chassis, the first and third conductive elements form a closed circuit, and when the substance is present in the front region, the fourth and first conductive elements forms a closed circuit.

21. The garment of claim 14 wherein the first and second conductive elements extend from the waist region to the crotch region without intersecting.

22. The garment of claim 14 wherein the first and second conductive elements form an open circuit and wherein, when a body fluid is present between the first and second conductive elements, the open circuit between the conductive elements is closed for activating a signaling device.

23. The garment of claim 14 wherein the chassis includes a signaling device receptacle adapted to contain the signaling device, the receptacle defining a pocket having an open edge, the open edge being elasticized.

24. The garment of claim 23 wherein the open edge is elasticized by a waist elastic member of the garment.

25. The garment of claim 14 wherein the chassis includes a signaling device receptacle adapted to contain the signaling device, the receptacle defining a pocket having an open edge having an open edge width and the pocket having a maximum width parallel to the open edge, the open edge width being less than the maximum width.

26. The garment of claim 14 wherein the open edge width is less than 90 percent the maximum width.

27. The garment of claim 14 wherein the chassis includes a signaling device receptacle adapted to contain the signaling device, the signaling device receptacle comprising a first material and a second material joined together, the first conductive element located on the first material, the second conductive element located on the second material.

\* \* \* \* \*